(12) United States Patent
Maurer et al.

(10) Patent No.: US 7,931,963 B2
(45) Date of Patent: Apr. 26, 2011

(54) COMPOSITE MATERIAL AND METHOD OF MAKING THE COMPOSITE MATERIAL

(75) Inventors: Myron J. Maurer, Saginaw, MI (US); Gavin D. Vogel, Lake Orion, MI (US); Byoung-Ho Choi, Uijeongbu-Si (KR); Warren H. Griffin, Saginaw, MI (US); Kalyan Sehanobish, Rochester, MI (US)

(73) Assignee: Dow Global Technologies LLC, Midland, MI (US)

( * ) Notice: Subject to any disclaimer, the term of this patent is extended or adjusted under 35 U.S.C. 154(b) by 273 days.

(21) Appl. No.: 12/129,828

(22) Filed: May 30, 2008

(65) Prior Publication Data

US 2008/0299379 A1  Dec. 4, 2008

Related U.S. Application Data

(60) Provisional application No. 60/933,054, filed on Jun. 4, 2007.

(51) Int. Cl.
 *B32B 3/26* (2006.01)

(52) U.S. Cl. ............... 428/314.8; 428/314.4; 428/304.4

(58) Field of Classification Search ............... 428/304.4, 428/314.4, 314.8
See application file for complete search history.

(56) References Cited

U.S. PATENT DOCUMENTS

| | | | |
|---|---|---|---|
| 2,795,008 A | 6/1957 | Lindemann et al. | |
| 2,899,708 A | 8/1959 | Donaldson et al. | |
| 3,231,524 A | 1/1966 | Simpson et al. | |
| 3,334,169 A | 8/1967 | Erceg et al. | |
| 3,482,006 A | 12/1969 | Carlson et al. | |
| 3,484,510 A | 12/1969 | Corazza | |
| 3,923,948 A | 12/1975 | Jackson et al. | |
| 4,359,160 A | 11/1982 | Myers et al. | |
| 4,420,448 A | 12/1983 | Krutchen | |
| 4,485,193 A | 11/1984 | Rubens et al. | |
| 4,575,117 A | 3/1986 | Uchida | |
| 5,149,726 A * | 9/1992 | Deblander | 521/143 |
| 5,244,928 A | 9/1993 | Smith et al. | |
| 5,340,844 A | 8/1994 | Welsh et al. | |
| 5,424,016 A | 6/1995 | Kolosowski | |
| 6,213,540 B1 | 4/2001 | Tusim et al. | |
| 6,420,442 B1 * | 7/2002 | Dietzen et al. | 521/82 |
| 7,520,559 B2 * | 4/2009 | Vo et al. | 296/187.01 |
| 2003/0225172 A1 | 12/2003 | Miller et al. | |
| 2004/0001945 A1 * | 1/2004 | Cate et al. | 428/316.6 |
| 2004/0135402 A1 | 7/2004 | Glunk et al. | |
| 2005/0192368 A1 | 9/2005 | Miller et al. | |
| 2006/0148919 A1 | 7/2006 | Maurer et al. | |

FOREIGN PATENT DOCUMENTS

| | | |
|---|---|---|
| EP | 0836032 | 4/1998 |
| WO | WO99/00236 | 1/1999 |
| WO | WO2005/039856 A1 | 5/2005 |
| WO | WO 2006053029 A1 * | 5/2006 |

* cited by examiner

*Primary Examiner* — Hai Vo
(74) *Attorney, Agent, or Firm* — Kevin J. Nilsen

(57) ABSTRACT

An improved energy absorbing member comprising, an thermoplastic cellular polymer in contact with a structural element such as a metal guard rail or automotive door, wherein the cellular polymer has an average cell size of at least about 0.75 mm and at least one of $C_E/C_T$, $C_V/C_T$ and $C_H/C_T$ is about 0.25 to about 0.4 said one of $C_E/C_T$, $C_V/C_T$ and $C_H/C_T$ having a compressive efficiency of at least 70% at a 60% strain, $C_E$, $C_V$ and $C_H$ being the compressive strength of the cellular polymer in each of three orthogonal directions E, V and H where one of these directions is the direction of maximum compressive strength in the foam and $C_T$ equals the sum of $C_E$, $C_V$ and $C_H$.

33 Claims, No Drawings

COMPOSITE MATERIAL AND METHOD OF MAKING THE COMPOSITE MATERIAL

CROSS-REFERENCE TO RELATED APPLICATION

This application claims the benefit of U.S. provisional patent application 60/933,054 filed Jun. 4, 2007.

FIELD OF THE INVENTION

The invention relates to crash energy absorbing polymeric foams in vehicles such as automobiles.

BACKGROUND OF THE INVENTION

Polymer foams are widely used in a variety of cushioning applications. Foams are commonly used in pillows, seating, mattresses and similar applications where softness and comfort are predominating factors. Foams are also used to cushion the contents of a package. In packaging, the foam, typically, only sees moderate strains due to jostling or dropping of the package and as a result is typically only elastically deformed (i.e., the foam springs back after being deformed, which is typically less than about 10% strain). Packaging foam also has little if any requirements related to the dimensions of the foam, but merely must cushion the contents against low impacts. Consequently, it is quite common for inexpensive expanded polystyrene bead foam and expanded cellulose based packaging peanuts to be used even though each of these are susceptible to considerable deformation due to temperature and humidity respectively.

In recent years, automobiles have been required to meet ever more stringent demands for mitigating occupant injury during crashes. To do so, automobiles have incorporated active systems such as air bags for frontal collisions. More recently, more and more attention has been paid to side crashes and head injuries from rollover accidents. These have employed side air bags, inflatable curtains (SABIC's) and have also started to employ foams that absorb energy not merely by elastically deforming, but by inelastically deforming (i.e., being crushed).

The vast majority of the foams used for automobile crash mitigation have been closed cell thermoset foams such as polyurethane/polyurea and their derivatives. These unfortunately, are difficult to recycle and to achieve crash efficiency they need to be friable causing them to possibly deteriorate over time, for example, due to vibration in a vehicle or weathering.

Other foams that have been employed have tended to be closed cell crystalline or semi-crystalline thermoplastic foams such as expanded polypropylene beads and polypropylene coalesced foam strands as described by U.S. Pat. No. 6,213,540. Each of these automobile energy absorbing foams tend to be expensive and of greater weight for the compressive energy absorbed than desired. For efficient absorption of crash energy, the foams have needed to have anisotropic strength due to anisotropic cells as described in U.S. Pat. No. 6,213,540 and US Pat. pub. 2006/0148919. Because of this orientation, these foams have needed to be oriented properly relative to the expected impact direction on the foam to get the expected crash absorption.

Accordingly, it would be desirable to provide an energy absorbing foam for vehicles that is inexpensive, has low weight, good energy absorbance and has uniform efficient crash absorption in multiple impact directions.

SUMMARY OF THE INVENTION

We have discovered a thermoplastic foam that may be used in any orientation while still achieving excellent compressive efficiency, which allows more energy to be dissipated over a given displacement. This surprising and desirable result is achieved while minimizing or essentially eliminating the friability of the foam. The minimization or elimination of the friability allows for a foam that does not degrade over time, for example, from vibration or weathering.

The invention is an energy absorbing member comprising, a thermoplastic cellular polymer in contact with a structural element, wherein the cellular polymer has an average cell size of at least about 0.75 mm and at least one of $C_E/C_T$, $C_V/C_T$ and $C_H/C_T$ is about 0.25 to about 0.4 said one of $C_E/C_T$, $C_V/C_T$ and $C_H/C_T$ having a compressive efficiency of at least 70% at a 60% strain, $C_E$, $C_V$ and $C_H$ being the compressive strength of the cellular polymer in each of three orthogonal directions E, V and H where one of these directions is the direction of maximum compressive strength in the foam and $C_T$ equals the sum of $C_E$, $C_V$ and $C_H$.

DETAILED DESCRIPTION OF THE INVENTION

The Energy Absorbing Member

The invention is an energy absorbing member comprising, a thermoplastic cellular polymer in contact with a structural element. The structural element of the energy absorbing member is any structure that supports or acts in concert with the cellular polymer (interchangeably referred to herein as "foam") to dissipate the energy of an impact such as a vehicular accident. Examples of structural elements are vehicular door panels, beams, dashes and roofs; helmet skins; and guard rails. Preferably, the structural element is a guard rail or roadway barrier including a race track guard rail or barrier, a door panel, door beam, dash or roof of an automobile or truck. It is understood that the structural member is to support and act as backing to the cellular polymer and is not meant to imply that the structural member is a component that necessarily is a structural element of a greater device (e.g., vehicle), even though it may be.

The energy absorbing member is also comprised of a thermoplastic cellular polymer. The thermoplastic cellular polymer may be semi-crystalline or amorphous. Amorphous means, as commonly understood in the art: (1) lacking a definite crystal structure; and (2) exhibiting a distinct and pronounced rubbery region. There, however, may be some very small ordered structure, but due to the size of such order, the techniques to measure such order, for example, fail to detect or is not substantially different than an amorphous material. For example, the ordered domains may be of such a small size that X-ray diffraction results in such diffuse scattering that if such domains were present they would be of a size of at most about 50 to 100 nanometers. Even though the polymer is amorphous, a small portion may display some localized order so long as a well defined rubbery region is not present. Illustratively, an X-ray diffraction pattern may display small peaks discernable above the noise of the X-ray technique. Semi-crystalline means herein, has a definite melting point and crystalline structure greater than described above for an amorphous polymer, but not with domains on the order of greater than millimeters. Examples of suitable semi-crystalline polymers include polyolefinic polymers such as polyethylene, polypropylene and copolymers thereof.

The polymer is understood to mean a synthetic organic polymer and may be any suitable thermoplastic polymer.

Exemplary suitable amorphous polymers include polystyrenic and polystyrenic copolymers. Polystyrenic means a polymer that is of a styrene monomer, derivative of a styrene monomer (e.g., a substituted styrene) or combination thereof. Examples of substituted styrenes are o-methylstyrene, m-methylstyrene, p-methylstyrene, 2,4-dimethylstyrene, 2,5-dimethylstyrene, p-tert-butylstyrene, p-chlorostyrene. Preferably, the polystyrenic polymer is polystyrene.

Polystyrenic copolymer means a copolymer of a styrenic monomer (styrene and derivative of a styrene monomer) described above and a comonomer that is not a styrenic monomer. Exemplary comonomers include acrylonitrile, poly(2,6-dimethyl-1,4-phenylene ether), methyl, ethyl or butyl acrylate, methacrylonitrile, maleimide, acrylic acid, methacrylic acid, maleic anhydride, itaconic anhydride or combination thereof. The comonomer is preferably acrylonitrile, maleic anhydride or combination thereof. More preferably, the comonomer is acrylonitrile.

Generally, the amount of styrenic monomer in the polystyrenic copolymer is at least about 50% by mole of the copolymer. Typically, the amount of comonomer is about 1% to 50% by mole of the polystyrenic copolymer. Preferably the amount of comonomer is at least 5%, more preferably at least about 10%, even more preferably at least about 20% and most preferably at least about 25% by mole of the polystyrenic copolymer.

A preferred polystyrenic copolymer is a styrene-acrylonitrile copolymer (SAN). The SAN copolymer may have 1% to 50% by weight of acrylonitrile. Preferably, the acrylonitrile is present in an amount of at least about 5%, more preferably at least 10%, and most preferably at least about 15% to preferably at most 40%, more preferably at most about 35% and most preferably at most about 30% by weight of the SAN copolymer.

The polymer may be of any useful weight average molecular weight (Mw). Illustratively, the Mw of a polystyrenic or polystyrenic copolymer may be from 10,000 to 1,000,000. The Mw of a polystyrenic or polystyrenic copolymer is desirably less than about 200,000, which surprisingly increases the efficiency yet does not deleteriously affect the friability. In ascending further preference, the Mw of a polystyrenic or polystyrenic copolymer is less than about 190,000, 180,000, 175,000, 170,000, 165,000, 160,000, 155,000, 150,000, 145,000, 140,000, 135,000, 130,000, 125,000, 120,000, 115,000, 110,000, 105,000, 100,000, 95,000, and 90,000. For clarity, molecular weight (MW) herein is reported as weight average molecular weight unless explicitly stated otherwise. The MW may be determined by any suitable method such as those known in the art.

In addition the polymer may also contain other additives so long as it remains an thermoplastic polymer. Examples of other additives include small amounts of cross-linking agents (e.g., divinyl benzene), colorants, UV-protectants, antioxidants, fillers, flame retardants, antistats, cell nucleation control agents and the like.

The polymer in the energy absorbing member is cellular. Cellular (foam) has the meaning commonly understood in the art in which a polymer has a substantially lowered apparent density comprised of cells that are closed or open. Closed cell means that the gas within that cell is isolated from another cell by the polymer walls forming the cell. Open cell means that the gas in that cell is not so restricted and is able to flow without passing through any polymer cell walls to the atmosphere. By convention, an open cell foam has 30% or more open cell content according to ASTM method D6226-05. A closed cell foam has less than 30% open cell content by that same method.

The cellular polymer is characterized by its surprising efficiency in at least one direction where at least one of $C_E/C_T$, $C_V/C_T$ and $C_H/C_T$ is 0.25 to 0.4 said one of $C_E/C_T$, $C_V/C_T$ and $C_H/C_T$ having a compressive efficiency of at least 70% at a 60% strain, $C_E$, $C_V$ and $C_H$ being the compressive strength of the cellular polymer in each of three orthogonal directions E, V and H where one of these directions is the direction of maximum compressive strength in the foam and $C_T$ equals the sum of $C_E$, $C_V$ and $C_H$.

The compressive strength is established when the compressive strength of the foam is evaluated in three orthogonal directions, E, V and H. These measured compressive strengths, $C_E$, $C_V$ and $C_H$, respectively, are related to the sum of these compressive strengths, $C_T$, such that at least one of $C_E/C_T$, $C_V/C_T$ and $C_H/C_T$, has a value of 0.25 to 0.4, preferably at least two have a value of 0.25 to 0.4 and most preferably, each of them has a value of 0.25 to 0.4. The sum of $C_E/C_T$, $C_V/C_T$ and $C_H/C_T$ will of course always equal 1. For a perfectly isotropic cellular polymer, each of $C_E/C_T$, $C_V/C_T$ and $C_H/C_T$, will equal 0.33. Therefore, if any of $C_E/C_T$, $C_V/C_T$ and $C_H/C_T$, exceeds 0.33, at least one of the other two will have a value of less than 0.33. In a preferred embodiment each of these ratios has a value from 0.30 to 0.37.

In a preferred embodiment, the foam is an extruded cellular polymer, wherein the direction E is the direction of extrusion, the direction V is the direction of vertical expansion of the cellular polymer after it exits the extrusion die, and the direction H is the direction of horizontal expansion of the cellular polymer after it exits the extrusion die. The directions E, V and H are arbitrary designations with respect to cellular polymers made in other processes. When the foam is an extruded cellular polymer, the V direction is taken as the one with the greatest compressive strength.

To achieve the surprising efficiency of the foam of this invention, the foam has cells that have an average cell size of at least about 0.75 mm in diameter as determined by a standard method such as ASTM D3576. The average cell size may be determined in each of the orthogonal directions E, V and H, to determine the average dimension in each of these directions ($D_E$, $D_V$ and $D_H$, respectively). The sum of $D_E$, $D_V$ and $D_H$ is calculated and designated $D_T$ cells (i.e., average cell size). The average cell size is generally from about 0.75 to about 10.0 mm. The average cell size may be and is typically desirably in ascending order at least 1, 1.1, 1.2, 1.3, 1.4 and 1.5 mm to at most, in ascending order, 4, 3.5, 3, 2.5 and 2 mm.

In a like manner, the ratios of the diameter in the E, V, and H directions may be determined as for the compressive strengths. Likewise, the same ratios that apply to the compressive strength ratios apply to the diameters herein and the cell shape may be used, via microscopy, used to quickly determine the direction of maximum compressive strength. That is the direction that has the largest diameter parallel to it, generally, corresponds to the direction having the greatest compressive strength.

The foam of the energy absorbing member is desirably not friable and surprisingly, the foam of the present invention may have a friability of less than 25% weight loss. The friability may be less than 20%, 15%, 10%, 9%, 8%, 7%, 6%, 5%, 4%, 3%, 2%, 1.5% or even 1% lost material. The friability may be determined by a standard method such as ASTM C421-00.

The foam may be comprised of open cells entirely or closed cells entirely and any combination between. For example, the foam may have 10%, 20%, 30%, 40%, 50%, 60%, 70%, 80% and even 90% open cells.

The foam in the energy absorbing member also desirably has the lowest possible density while providing sufficient energy absorption, which typically is a function of the specific impact expected. In impact-absorbing members that are intended for head injury abatement applications, such as headliner countermeasures, helmets and the like, the cellular polymer also advantageously exhibits a compressive strength of at least 250 kPa, preferably of at least 290 kPa at 25% strain, up to about 700 kPa, especially up to about 600 kPa, as measured on a 25-50 mm thick sample at a strain rate of 0.08 s$^{-1}$. For these applications, the cellular polymer advantageously has a density of no greater than about 3.5 pounds/cubic foot (56 kg/m$^3$), preferably no greater than about 2.5 pounds/cubic foot (40 kg/m$^3$), more preferably no greater than about 2.35 pounds/cubic foot (37.6 kg/m$^3$). Preferably, the density is at least about 1.5 pounds/cubic foot (24 kg/m$^3$). An especially preferred density is from about 1.75 to about 2.2 pounds/cubic foot (28-35.2 kg/m$^3$). It has been found that cellular polymers having these compressive strengths and densities tend to have particularly low HIC(d) values, measured according to FMVSS 201(U). A particularly preferred cellular polymer for use in head injury abatement applications will have, when tested as indicated above, a compressive strength at 25% strain of 290-600 kPa, a density of 1.5 to 2.2 pounds/cubic foot (24-35.2 kg/m$^3$), and an elastic limit of from 3-10% strain.

For pelvic injury protection abatement applications, such as pelvic bolsters and the like, the cellular polymer also advantageously exhibits a compressive strength of at least 250 kPa, preferably of at least 350 kPa at 25% strain, up to about 1000 kPa, especially up to about 900 kPa, measured on a 25-50 mm thick sample at a strain rate of 0.08 s$^{-1}$. For these applications, the cellular polymer advantageously has a density of no greater than 5 pounds/cubic foot (80 kg/m$^3$) and preferably no greater than 4.5 pounds/cubic foot (72 kg/m$^3$). Preferably, the density is at least 2.0 pound/cubic foot (32 kg/m$^3$). An especially preferred density is from about 2.1 to about 4.0 pounds/cubic foot (34-64 kg/m$^3$). These stiffer cellular polymers still tend to exhibit a desired nearly constant compressive stress over a wide strain range. A particularly preferred cellular polymer for use in pelvic injury protection applications will have, when tested as indicated above, a compressive strength at 25% strain of 300-900 kPa, a density of 2.1 to 4.0 pounds/cubic foot (34-64 kg/m$^3$), and an elastic limit of from 3-10% strain.

In thoracic abatement applications, such as thorax bolsters and the like, the cellular polymer also advantageously exhibits a compressive strength, in the direction of expected impact, of at least 150 kPa, preferably of at least 200 kPa at 25% strain, up to about 700 kPa, especially up to about 500 kPa, measured on a 25-50 mm thick sample at a strain rate of 0.08 s$^{-1}$. For these applications, the cellular polymer advantageously has a density of no greater than 3.0 pounds/cubic foot (48 kg/m$^3$), preferably no greater than 2.0 pounds/cubic foot (32 kg/m$^3$). Preferably, the density is at least 1.25 pounds/cubic foot (20 kg/m$^3$). An especially preferred density is from about 1.5 to about 2.0 pounds/cubic foot (24-32 kg/m$^3$). These more flexible cellular polymers still tend to exhibit the desired nearly constant compressive stress over a wide strain range. A particularly preferred cellular polymer for use in thoracic injury protection applications will have, when tested as indicated above, a compressive strength at 25% strain of 150-400 kPa, a density of 1.5 to 2.0 pounds/cubic foot (24-32 kg/m$^3$), and an elastic limit of from 3-10% strain.

The cellular polymer has a compressive efficiency of at least 70%, preferably at least 75%, more preferably at least 78%, and preferably at least 80% at 60% strain in at least one direction V, E, or H where $C_V$, $C_E$, or $C_E$ over $C_T$ is from 0.25 to 0.4. Likewise, it is preferred that said direction has a compressive efficiency of at least 60%, more preferably at least 65%, even more preferably at least 70% and most preferably at least 75% at 65% strain. Compressive efficiencies of 85% or more can be obtained with the invention at 60-65% strain. Preferably, at least two directions have the aforementioned efficiency and ratio and most preferably all three of the directions have the aforementioned efficiency and ratio.

Compressive efficiency is computed by compressing the foam at a strain rate of 0.08 s$^{-1}$ in the manner described before, and recording instantaneous load and crosshead displacement. Transient engineering stress is calculated by dividing the instantaneous load by the original cross-section area of the foam specimen normal to the direction of compression. Transient engineering strain is calculated by dividing the change in thickness by the original thickness. Compressive efficiency is then calculated using the relationship $$\text{Efficiency}(\%) = 100\% \cdot \left( \frac{\int_0^\varepsilon \sigma \cdot \partial \varepsilon}{\sigma_{max} \cdot \varepsilon} \right)$$

where σ represents the instantaneous engineering stress, typically in MPa, ε represents the engineering strain and $\sigma_{max}$ represents the maximum engineering stress achieved in the same units as the instantaneous engineering stress. Illustratively, when viewing an engineering stress vs. engineering strain curve with the stress on the vertical (i.e., y) axis, a 100% efficient curve would appear rectangular whereas a 50% efficient curve would appear as a right triangle, where the stress builds linearly. Such a rectangular curve is shown by graph 1 of FIG. 1 of U.S. Pat. publ. 2006/0148919.

The cells of the cellular polymer may have an average size of from about 0.75 to about 10.0 mm, as measured by ASTM D-3576-98. The cell size may be, generally, in ascending order at least 0.8, 0.9, 1, 1.1, 1.2, 1.3, 1.4 and 1.5 mm to at most, in ascending order, 4, 3.5, 3, 2.5 and 2 mm.

The effective glass temperature of the foam, as opposed to the glass transition temperature of the native thermoplastic polymer, is the glass transition temperature of the foam in the energy absorbing member and the effective glass temperature is used to take into consideration, for example, the plasticizing effect that a blowing agent may have on the glass transition temperature of the polymer of the foam. The invention is particularly useful for thermoplastic polymers where the effective glass transition temperature of the foam is about 75° C. to about 140° C. The invention is particularly useful, because it allows foams with low glass transition temperature, which might otherwise bloat or expand upon heating to be dimensionally stable at higher temperatures. Preferably, the effective glass transition temperature is at least about 80° C., more preferably at least about 85° C., even more preferably at least about 90° C. and most preferably at least about 95° C. to preferably at most about 135° C., more preferably at most about 130° C., even more preferably at most about 125° C., and most preferably at most about 120° C.

The effective glass temperature of the foam can be determined with the method ASTM D4065-01 Dynamic Mechanical Properties Determination. The elastic and loss moduli of the foam are measured with dynamic thermomechanical analyzer instruments, such as Rheometric Scientific RDA III Dynamic Mechanical Analyzer or Rheometrix Dynamic Mechanical Thermal Analyser RSA II, made by Rheometric Scientific Inc, TA Instruments Group, New Castle, Del. These moduli are a function of temperature and change rapidly at a particular temperature range. The regions of rapid moduli change are normally referred to as transition regions and the Tg is determined as per the standard.

The foam of the energy absorbing member, invariably is formed using a blowing agent and as such typically has some residual blowing agent in the cells or that is solubilized within the polymer itself. The foam may have any suitable blowing agent such as a volatile aliphatic hydrocarbon, chlorinated hydrocarbon, fluorinated hydrocarbon, chlorofluorinated hydrocarbon, gas present in the atmosphere (e.g., oxygen, nitrogen, carbon dioxide, hydrogen, water vapor, helium and the like) or combination thereof.

Examples of a volatile hydrocarbon include ethane, ethylene, propane, propylene, butane, butylenes, isobutene, pentane, cyclopentane, isopentane, hexane, heptane, or mixture thereof. Examples of chlorinated hydrocarbons, fluorinated hydrocarbons and chlorofluorinated hydrocarbons include methyl chloride, Dichlorodifluoromethane, Octafluorocyclobutane, Chlorodifluoromethane, 1,2-Dichlorotetrafluoroethane, 1,1-Dichlorotetrafluoroethane, Pentafluoroethane, 2-Chloro-1,1-difluoroethane, 2-Chloro-1,1,1-trifluoroethane, 1,1,1,2-Tetrafluoroethane, 1,1,1-Trifluoroethane, 1,1, 1-Trifluoropropane, Trichlorotrifluoroethane, Difluoromethane, 2-Chloro-1,1,1,2-tetrafluoroethane, 2,2-Difluoropropane, Ethyl chloride or a mixture thereof.

Illustratively, polystyrenic and polystyrenic copolymers typically have employed chlorofluoro hydrocarbons as the gas blowing agent. These tend to plasticize the polymer resulting in a lower effective glass transition temperature, which may cause the inability of the foam to be dimensionally stable. These also have tended, because of their slow diffusion rate, to form foams where the average gas pressure is greater than 1 atmosphere even after the foam has been aged for a long period of time. Consequently, it is preferred that at least one blowing agent or one component of the mixture of blowing agents has a substantially faster diffusion rate through the foam than air to facilitate the formation of a foam having the aforementioned average gas pressure. Substantially faster in this context means that the diffusion rate of the blowing agent is at least about 2 times faster than the diffusion rate of air. Diffusion of air is taken as the average diffusion rate of oxygen and nitrogen weighted by the presence of each in air. Preferably, the diffusion rate of the blowing agent is at least about 3 times, more preferably at least 4 times, even more preferably at least 5 times and most preferably at least 10 times faster than the diffusion rate of air.

Because, for example, of environmental concerns, a particularly desirable embodiment of the invention is when the amorphous thermoplastic polymer is the polystyrenic or polystyrenic copolymer and the blowing agent is comprised of carbon dioxide, water or combination thereof. Preferably for this embodiment, the primary blowing agent is carbon dioxide.

Forming the Energy Absorbing Member

The energy absorbing member may be made by any suitable methods such as those that follow. The thermoplastic polymer and a blowing agent are mixed together. Any suitable method of mixing the polymer and blowing agent may be used such as those known in the art. For example, the blowing agent may be injected into polymer that has been heated within an extruder such as described in U.S. Pat. Nos. 3,231,524; 3,482,006, 4,420,448 and 5,340,844 or the blowing agent may be added to polymer beads, typically under pressure, as described by U.S. Pat. No. 4,485,193 and each of the U.S. patents this patent cites at col. 3, lines 6-13.

After the polymer and the blowing agent are mixed, the polymer and blowing agent are formed into a shape, which may be a final shape or an interim shape and may be done by any suitable method such as those known in the art (e.g., extruded expanded planks and expanded bead foam). For example, when using extrusion, a plank of foam may be formed, which is later wire cut into a more complex final shape or the board may be cut into useful shapes that are then thermoformed into a more desired final shape.

Such thermoforming, which is well known in the art and is described, for example, by U.S. Pat. Nos. 2,899,708; 3,334, 169; 3,484,510; 3923,948 and 4,359,160, may be done at anytime after forming a shaped foam, but is preferably done after the shaped foam has realized a particular gas pressure. The average gas pressure of the closed cells during thermoforming may be any useful pressure, but advantageously is a lower pressure, because of the compaction of the foam during thermoforming, which can raise the pressure. Illustratively, the gas pressure of the foam is generally desirable to be at most about 1 atmosphere, preferably at most about 0.95 atmosphere 0.9, more preferably at most about 0.85 and most preferably at most about 0.8 to at least about 0.5.

In a preferred method, an extruded foam plank is formed, which is then planed to create open cells at the surface of the extruded foam plank and/or perforated. It is preferred that at least both the top and bottom of a foam plank is planed (i.e., the large surfaces of a plank, or for example, the 4'×8' surfaces of a 4'×8'×1"plank). When perforating the plank, the perforations may extend through the depth of the plank or form blind holes. The perforations may be made in a like manner as described by U.S. Pat. No. 5,424,016 used to release entrapped flammable hydrocarbon gases (e.g., isobutane and pentane) from foam planks.

In addition, if desired, the foam may be treated at a temperature above ambient to realize a useful cell gas pressure for forming the part, but below a temperature where the foam might distort, which is readily determinable depending on the particular polymer used. The foam may also be exposed to differing atmospheres, for example the atmosphere may be dried air when water is used as a blowing agent. The pressure of the atmosphere surrounding the shaped foam may also be below atmosphere (vacuum) or at an elevated pressure so long as the vacuum or elevated pressure is not so great that the foam distorts. Preferably, for convenience, the pressure is ambient pressure and the atmosphere is air.

The foam may also have a decorative lining or impervious membrane attached to a portion of the surface or the entire surface of the foam. The impervious membrane may be of any material that limits or ceases the migration of gases into or out of the foam. Such films may be applied by any suitable method such as those known in the art (e.g., sputtering, chemical vapor deposition, adhering foils, films or sheets using an adhesive or thermally fusing). Examples of impervious membranes include metallic foils (e.g., silver, aluminum, ferrous based foils such as steel foils) and plastic films such as polyethylene terephthalate (PET) film, Polyamide films or combinations thereof.

Finally, to make the energy absorbing member, the foam is attached to the structural member. The treated shaped foam may be directly foamed, for example, into a cavity in the structural member when using, for example, an expandable bead foam in a helmet skin or in a door panel. The cavity may be designed into the structural element to facilitate attachment of the foam. The foam may also be attached to the structural element by any suitable method such as those known in the art including, for example, mechanically (e.g., fasteners) or chemically (e.g., adhesives and heating the structural member to a temperature sufficiently such that the foam fuses to the structural member when the foam is brought into contact with the structural element and fusing by applying a solvent to a surface of the foam and contacting it to the structural member).

The following Claims, even though they may not explicitly depend from one another, the invention contemplates any combination of one or more embodiments of any one claim combined with any one or more claims.

Test Methods

Density: Foam density was determined from the weight and geometric volume.

Cell Size: The cell size of the foams were determined by the line intercept method as described by ASTM D3576-98 in each of the orthogonal direction E, V, and H and the average cell size determined therefrom.

Friability: The friability was determined using ASTM C421-00

Compressive Strength: The compressive strength was determined rectangular foam samples using a Materials Test System Alliance RT-50 equipped with a 50 kN load cell and linear variable differential transducer (LVDT) run using a strain rate of 0.08 $s^{-1}$. The compressive strength was determined individually for three orthogonal directions where the "E" direction corresponds with the extruded direction for a foam made by extrusion, "V" corresponds to the rise direction after the foam exits the extrusion die (parallel to the force of gravity) and "H" corresponds to horizontal expansion of the foam after it exits the extrusion die. By definition, compressive strength is the maximum value of either 1) the yield stress or 2) stress at 10% strain.

ILLUSTRATIONS

Illustration 1

A 10"×20"×109" STYROFOAM extruded foam polystyrene pipe billet commercially available from The Dow Chemical Company was obtained for test purposes made in like manner as described in U.S. Pat. No. 5,244,928, example 3. The foam is made using HCFC 142B (1-chloro-1,1-difluoroethane)as the blowing agent. The alkenyl aromatic polymer employed was a polystyrene with a 168,000 weight average molecular weight as measured by size exclusion chromatography. The foam was analyzed and tested as described above. The foam's characteristics and test results are shown in Table 1.

Illustration 2

A 10.375"×24"×108.125" extruded polystyrene floral and craft foam billet commercially available from The Dow Chemical Company was obtained. The foam is made using HCFC 142B (1-chloro-1,1-difluoroethane)as the blowing agent and in a like manner as described in U.S. Pat. No. 5,244,928, example 1. The alkenyl aromatic polymer employed was a polystyrene with a 168,000 weight average molecular weight as measured by size exclusion chromatography. The foam was analyzed and tested as described above. The foam's characteristics and test results are shown in Table 1.

Comparative Illustration 1

A 2"×48"×96" plank of R-7.8 CELLOFOAM™ expanded polystyrene (EPS) bead foam, produced by Cellofoam North America Incorporated, was purchased from Lowe's Home Center, Inc. in Midland, Mich. (Item No. 15357). The foam, because it was a bead foam had a bimodal cell size correlating to the pores between beads of foam that fused together upon expansion and the cells within the beads themselves. The cell size of the cells within the foam are reported in Table 1 along with the rest of this foam's characteristics. The foam was blown with pentane (CAS No. 109-66-0) as reported in Section 2 of the Material Safety Data Sheet (MSDS).

Comparative Illustration 2

A 2"×48"×96" plank of R-10 STYROFOAM SCOREBOARD™ extruded polystyrene (XPS) sheathing foam, produced by The Dow Chemical Company, Midland, Mich. was purchased from Lowe's Home Center, Inc. in Midland, Mich. (Item No. 14541) and tested as described above with the results shown in Table 1. This foam was made from a polystyrene having a MW of about 168,000 and blown using HCFC 142B (1-chloro-1,1-difluoroethane).

Comparative Illustration 3

ETHAFOAM™ 220, available from The Dow Chemical Co., Midland, Mich., was tested as described above with the results shown in Table 1. This foam is an extruded polyethylene foam. The polyethylene had a MW of about 137,000 and was blown using isobutane.

Comparative Illustration 4

IMPAXX™ 300, available from The Dow Chemical Co., Midland, Mich., was tested as described above with the results shown in Table 1. This foam is an extruded polystyrene foam. The polystyrene had a MW of about 146,000 and was blown using carbon dioxide.

Comparative Illustration 5

STYROFOAM™ FB-X, available from The Dow Chemical Co., Midland, Mich., was tested as described above with the results shown in Table 1. This foam is an extruded polystyrene foam. The polystyrene had a MW of about 146,000 and was blown using HFC 134A (1,1,1,2-tetrafluoroethane).

Comparative Illustration 6

Friable polyurethane (PU) foam specimens were obtained from a pelvic absorber countermeasure utilized in the 2006 model vehicle of a Ford Freestyle. The original dimensions of the complex, 3-D formed part was approximately 250 mm in length, 200 mm wide, and 60-75 mm in thickness. Simplified 50 mm cube samples were prepared from the full part using a common band saw. The specimens were labeled to reflect the appropriate orientation (i.e. vert.=thickness, hor.=width, and ext.=length), and tested as described above with the average results shown in Table 1.

TABLE 1

| Ill. | Test Direction | Density (kg/m3) | Cell Size (mm) | Friability (% Lost) | Comp. Strength (kPa) | Comp. Bal. (R) | Efficiency @ 60% Strain |
|---|---|---|---|---|---|---|---|
| 1 | Vert. | 30.2 | 0.88 | 2.87 | 213 | 0.39 | 76.1 |
|   | Ext. | 30.3 |  |  | 218 | 0.40 | 75.7 |
|   | Hor. | 30.3 |  |  | 112 | 0.21 | 57.7 |
| 2 | Vert. | 31.4 | 1.98 | 4.59 | 273 | 0.40 | 88.2 |
|   | Ext. | 31.2 |  |  | 224 | 0.33 | 82.3 |
|   | Hor. | 31.2 |  |  | 178 | 0.26 | 66.7 |
| Comp. 1 | Vert. | 14.18 | 0.33 | 0.72 | 88 | 0.33 | 54.4 |
|   | Ext. | 14.27 |  |  | 88 | 0.33 | 55.1 |
|   | Hor. | 14.28 |  |  | 93 | 0.34 | 55.4 |
| Comp. 2 | Vert. | 25.33 | 0.23 | 1.33 | 281 | 0.44 | 70.8 |
|   | Ext. | 23.84 |  |  | 214 | 0.33 | 63.3 |
|   | Hor. | 23.71 |  |  | 150 | 0.23 | 57.1 |
| Comp. 3 | Vert. | 37.6 | 1.21 | 0.50 | 70 | 0.30 | 51.2 |
|   | Ext. | 38.2 |  |  | 55 | 0.23 | 47.7 |
|   | Hor. | 38.0 |  |  | 111 | 0.47 | 58.8 |
| Comp. 4 | Vert. | 31.2 | 0.35 | 1.34 | 465 | 0.63 | 87.2 |
|   | Ext. | 31.2 |  |  | 151 | 0.20 | 59.9 |
|   | Hor. | 31.1 |  |  | 127 | 0.17 | 59.2 |
| Comp. 5 | Vert. | 36.5 | 0.98 | 1.05 | 403 | 0.42 | 79.2 |
|   | Ext. | 36.6 |  |  | 299 | 0.31 | 64.9 |
|   | Hor. | 36.5 |  |  | 261 | 0.27 | 67.1 |
| Comp. 6 | Vert. | 37.8 | 0.54 | 36.38 | 127 | 0.28 | 73.1 |
|   | Ext. | 38.3 |  |  | 161 | 0.36 | 86.4 |
|   | Hor. | 38.5 |  |  | 162 | 0.36 | 83.2 |

Examining Table 1, comparative 1, even though it displays good isotropic compressive strengths (R values near 0.33), its compressive efficiency in all directions V, E and H are substantially less than Example 1, which has two R values that are 0.3 to 0.4 that have compressive efficiencies greater than 70% at 60% strain. This improved efficiency for isotropic values of R is believed to be primarily due to the larger cell size. The effect of the cell size is also shown by the increased efficiency as the cell size increases from Illustration 1 to Illustration 2 (increase in efficiency from about 75% to 85%). Also in a similar manner, comparative Illustrations 2 and 4 made by the same process (extruded polystyrene foam) as Illustrations 1 and 2, had a substantially smaller cell size and did not display the same desirable compressive efficiency in multiple directions.

Next, examining, Comparative Illustration 3, this foam even though it has a larger cell size displays low compressive efficiencies in all cases, even when the R value exceeds 0.4. This is believed to be due to it being a semi-crystalline thermoplastic polymer.

With regard to Comparative Illustration 5, even though this foam is an extruded polystyrene foam and quite similar to Illustration 1, it did not display the desired compressive efficiency at R values of 0.25 to 0.4. This is believed to be due to the differing blowing agents and greater anisotropy of Comparative Illustration 5. In other words, it appears that, when using a fluoro-hydrocarbon blowing agent and a polystyrenic or polystyrenic copolymer, it may be desirable, in general, to use a hydro-fluoro-chloro-carbon (HCFC) blowing agent over a hydro-fluoro-carbon (HFC).

To further illustrate the invention, extruded polystyrene and polystyrene copolymers were made, while maintaining the density of the foams made.

Illustration 3

An extruded polystyrene foam sample was prepared according to the process of the present invention using 9.5 pph (parts per hundred by weight). HCFC 142B (1-chloro-1,1-difluoroethane) as the primary blowing agent and 3.5 pph HCFC 22 as the secondary blowing agent. The polystyrene was extruded using a 2½ inch (64 mm) single-screw extruder, a mixer, coolers, and a die in series at 91 kg/h polystyrene at a foaming temperature of about 128° C. The alkenyl aromatic polymer employed was a polystyrene with a 168,000 weight average molecular weight as measured by size exclusion chromoatography. Additives were hexabromocyclododecane (HBCD) at 0.8 pph, barium stearate at 0.05 pph, tetrasodium pyrophosphate at 0.05 pph, and linear low density polyethylene (LLDPE) at 0.20 pph. The foam was analyzed and tested as described above. The foam's characteristics and compressive efficiency in each direction is shown in Table 2.

Illustration 4

An extruded polystyrene foam sample was prepared according to the process of the present invention using 2.0 pph carbon dioxide ($CO_2$) as the primary blowing agent and 1.7 pph water ($H_2O$) as the secondary blowing agent. The same extruder as in Illustration 3 was used, but at 102 kg/h and a foaming temperature of about 139° C. The alkenyl aromatic polymer employed was ninety parts by weight polystyrene, MW of 168,000, blended with 10 parts by weight of styrene—acrylic acid (SAA) copolymer, MW of 17,250. The SAA copolymer had approximately 73% styrene and 27% acrylic acid by weight respectively. Additives were hexabromocyclododecane (HBCD) at 0.8 pph, calcium stearate at 0.05 pph, tetrasodium pyrophosphate at 0.05 pph, and linear low density polyethylene (LLDPE) at 0.20 pph. The foam was analyzed and tested as described above. The foam's characteristics and compressive efficiency in each direction is shown in Table 2.

Illustration 5

The same procedure as described for Illustration 4 was used to make this foam except that the blend was 80 parts by weight polystyrene and 20 parts by weight of the SAA copolymer. The characteristics and compressive efficiency in each direction is shown in Table 2.

Illustration 6

An extruded polystyrene foam sample was prepared according to the process of the present invention using 2.0 pph carbon dioxide ($CO_2$) as the primary blowing agent and 1.7 pph water ($H_2O$) as the secondary blowing agent. The foam structure produced had the desired large average cell size. The same extruder as described in Illustration 3 was used with the throughput being 91 kg/hr polystyrene and the foaming temperature being 123° C. The alkenyl aromatic polymer employed was 85% by weight styrene—15% by weight acrylonitrile "SAN" copolymer having a MW of 84,100. Additives were hexabromocyclododecane (HBCD) at 1.1 pph, barium stearate at 0.016 pph, tetrasodium pyrophosphate at 0.10 pph, and linear low density polyethylene (LLDPE) at 0.20 pph. The foam was analyzed and tested as described above. The foam's characteristics and compressive efficiency in each direction is shown in Table 2.

Illustrations 7-11

The same procedure was used as described for Illustration 6 except that the MW of the SAN copolymer and/or blowing agents were changed as shown in Table 2. The characteristics and compressive efficiency in each direction is shown in Table 2. The foaming temperature of each these was about 135° C. to 139° C.

TABLE 2

| Ill. | Polymer | $M_w$ | $CO_2$ (pph) | $H_2O$ (pph) | HCFC 142b (pph) | HCFC 22 (pph) | Density (kg/m³) | Cell Size (mm) | Test Dir. | Comp. Str. (kPa) | R | $\epsilon = 60\%$ | $\epsilon = 70\%$ |
|---|---|---|---|---|---|---|---|---|---|---|---|---|---|
| 3 | PS | 168,000 | 0 | 0 | 9.5 | 3.5 | 29.4 | 1.55 | Vert. | 236 | 0.34 | 69.6 | 59.7 |
|   |   |   |   |   |   |   |   |   | Hor. | 253 | 0.37 | 71.6 | 60.2 |
|   |   |   |   |   |   |   |   |   | Ext. | 197 | 0.28 | 64.6 | 54.3 |
| 4 | 90% PS | 168,000 | 2.0 | 1.7 | 0 | 0 | 28.5 | 2.08 | Vert. | 131 | 0.41 | 85.7 | 84.6 |
|   | 10% SAA | 17,250 |   |   |   |   |   |   | Hor. | 111 | 0.33 | 93.0 | 92.2 |
|   |   |   |   |   |   |   |   |   | Ext. | 79 | 0.25 | 89.4 | 82.8 |
| 5 | 80% PS | 168,000 | 2.0 | 1.7 | 0 | 0 | 29.3 | 2.09 | Vert. | 203 | 0.36 | 85.1 | 72.5 |
|   | 20% SAA | 17,250 |   |   |   |   |   |   | Hor. | 161 | 0.33 | 92.8 | 65.5 |
|   |   |   |   |   |   |   |   |   | Ext. | 163 | 0.31 | 91.2 | 62.9 |
| 6 | SAN | 84,100 | 2.0 | 1.7 | 0 | 0 | 28.8 | 1.86 | Vert. | 149 | 0.34 | 91.5 | 91.6 |
|   |   |   |   |   |   |   |   |   | Hor. | 173 | 0.39 | 91.0 | 91.5 |
|   |   |   |   |   |   |   |   |   | Ext. | 123 | 0.27 | 90.5 | 71.4 |
| 7 | SAN | 84,100 | 2.5 | 1.7 | 0 | 0 | 28.4 | 1.69 | Vert. | 109 | 0.31 | 92.9 | 92.6 |
|   |   |   |   |   |   |   |   |   | Hor. | 149 | 0.45 | 87.1 | 87.1 |
|   |   |   |   |   |   |   |   |   | Ext. | 83 | 0.24 | 91.5 | 72.0 |
| 8 | SAN | 111,500 | 2.0 | 1.7 | 0 | 0 | 29.6 | 2.29 | Vert. | 176 | 0.37 | 86.9 | 62.2 |
|   |   |   |   |   |   |   |   |   | Hor. | 191 | 0.37 | 89.2 | 69.9 |
|   |   |   |   |   |   |   |   |   | Ext. | 129 | 0.27 | 73.7 | 53.6 |
| 9 | SAN | 111,500 | 2.5 | 1.7 | 0 | 0 | 28.2 | 2.33 | Vert. | 232 | 0.32 | 79.7 | 62.5 |
|   |   |   |   |   |   |   |   |   | Hor. | 247 | 0.37 | 82.6 | 64.6 |
|   |   |   |   |   |   |   |   |   | Ext. | 212 | 0.31 | 69.0 | 57.8 |
| 10 | SAN | 155,800 | 2.0 | 1.7 | 0 | 0 | 34.0 | 2.29 | Vert. | 236 | 0.32 | 71.6 | 54.9 |
|   |   |   |   |   |   |   |   |   | Hor. | 257 | 0.40 | 83.9 | 57.0 |
|   |   |   |   |   |   |   |   |   | Ext. | 176 | 0.27 | 65.6 | 49.7 |
| 11 | SAN | 155,800 | 2.5 | 1.7 | 0 | 0 | 31.1 | 2.97 | Vert. | 237 | 0.31 | 70.8 | 56.8 |
|   |   |   |   |   |   |   |   |   | Hor. | 276 | 0.38 | 72.5 | 58.9 |
|   |   |   |   |   |   |   |   |   | Ext. | 227 | 0.31 | 63.1 | 50.5 |

PS = polystyrene
SAN = styrene-acrylonitrile
SAA = styrene-acrylic acide

From Table 2, it appears to be desirable to have a lower MW polymer when forming the foam useful for this invention (see, for example, Illustrations 6, 8 and 10 or 7, 9 and 11). The Illustrations with copolymer also demonstrate that compressive efficiencies in all directions even at 70% strain may be greater than 70% or even 80%.

The following Claims, even though they may not explicitly depend from one another, the invention contemplates any combination of one or more embodiments of any one claim combined with any one or more claims.

What is claimed is:

1. An energy absorbing member comprising, an thermoplastic cellular polymer attached to a structural element, wherein the cellular polymer has an average cell size of at least about 0.75 mm and each one of $C_E/C_T$, $C_V/C_T$, and $C_H/C_T$ is about 0.25 to about 0.37 with at least one of $C_E/C_T$, $C_V/C_T$, and $C_H/C_T$ having a compressive efficiency of at least 70% at a 60% strain, $C_E$, $C_V$, and $C_H$ being the compressive strength of the cellular polymer in each of three orthogonal directions E, V and H where $C_T$ equals the sum of $C_E$, $C_V$, and $C_H$, wherein the structural element is a helmet skin, a vehicular door panel, a vehicular door beam, a vehicular roof, or a vehicular dash.

2. The energy absorbing member of claim 1, wherein the cellular polymer has a density no greater than about 2.5 pounds per cubic foot.

3. The energy absorbing member of claim 2, wherein the structural element is a vehicular door panel, or a vehicular door beam.

4. The energy absorbing member of claim 1, wherein the thermoplastic cellular polymer is a polystyrenic polymer or polystyrenic copolymer.

5. The energy absorbing member of claim 4, wherein the thermoplastic cellular polymer is the polystyrenic polymer.

6. The energy absorbing member of claim 5, wherein the polystyrenic polymer is polystyrene.

7. The energy absorbing member of claim 4, wherein the thermoplastic cellular polymer is the polystyrenic copolymer.

8. The energy absorbing member of claim 7, wherein the polystyrenic copolymer is a copolymer of styrenic monomer and a comonomer selected from the group consisting of acrylonitrile, poly(2,6-dimethyl-1,4-phenylene ether), methyl acrylate, methacrylonitrile, maleimide, acrylic acid, methacrylic acid, maleic anhydride, itaconic anhydride and combination thereof.

9. The energy absorbing member of claim 8, wherein the comonomer is acrylonitrile.

10. The energy absorbing member of claim 9, wherein the acrylonitrile is present in amount of about 1% to about 35% by weight of the thermoplastic cellular polymer.

11. The energy absorbing member of claim 10, wherein the acrylonitrile is present in an amount of at most about 20%.

12. The energy absorbing member of claim 11, wherein the acrylonitrile is present in an amount of at most about 15%.

13. The energy absorbing member of claim 1, wherein the thermoplastic cellular polymer is amorphous and contains a residue of a blowing agent.

14. The energy absorbing member of claim 13, wherein the blowing agent is a volatile aliphatic hydrocarbon, carbon dioxide, water or combination thereof.

15. The energy absorbing member of claim 14, wherein the blowing agent is ethane, ethylene, propane, propylene, butane, butylenes, isobutene, pentane, neopentane, isopentane, hexane, heptane, carbon dioxide, water or combination thereof.

16. The energy absorbing member of claim 15, wherein the blowing agent is comprised of carbon dioxide, water or combination thereof.

17. The energy absorbing member of claim 1, wherein each of $C_E/C_T$, $C_V/C_T$ and $C_H/C_T$ is 0.3 to 0.37.

18. The energy absorbing member of claim 17, wherein each $C_E/C_T$, $C_V/C_T$ and $C_H/C_T$ have compressive efficiency that is at least 70% at a 60% strain.

19. The energy absorbing member of claim 17, wherein each has a compressive efficiency of at least 70% at 60% strain.

20. The energy absorbing member of claim 19, wherein the compressive efficiency is at least 75%.

21. The energy absorbing member of claim 13, wherein the blowing agent is carbon dioxide, water or combination thereof.

22. The energy absorbing member of claim 1, wherein the compressive efficiency is at least 75%.

23. The energy absorbing member of claim 22, wherein the compressive efficiency is at least 80%.

24. The energy absorbing member of claim 1, wherein at least about 70% of the cells of the thermoplastic cellular polymer are closed cells.

25. The energy absorbing member of claim 24, wherein at least about 90% of the cells of the thermoplastic cellular polymer are closed cells.

26. The energy absorbing member of claim 1, wherein at least two of $C_E/C_T$, $C_V/C_T$ and $C_H/C_T$ have compressive efficiency that is at least 70% at a 60% strain.

27. The energy absorbing member of claim 26, wherein the compressive efficiency is at least 75% at a 60% strain.

28. The energy absorbing member of claim 1, wherein the friability of the cellular polymer has a friability of at most about 10% lost material by weight.

29. The energy absorbing member of claim 28, wherein the friability is at most 5% lost material by weight.

30. The energy absorbing member of claim 1, wherein the thermoplastic cellular polymer is an amorphous thermoplastic polymer.

31. The energy absorbing member of claim 1, wherein the thermoplastic cellular polymer is a semi-crystalline thermoplastic polymer.

32. The energy absorbing member of claim 31, wherein the semi-crystalline thermoplastic polymer is a polyolefinic polymer.

33. The energy absorbing member of claim 32, wherein the polyolefinic polymer is polyethylene, polypropylene or copolymers thereof.

* * * * *